(12) United States Patent
Scott et al.

(10) Patent No.: US 7,041,315 B2
(45) Date of Patent: May 9, 2006

(54) PECTIN FILM COMPOSITIONS

(75) Inventors: Robert Anthony Scott, Sint-Niklaas (BE); Dominique Cade, Colmar (FR); Xiongwei He, Andolsheim (FR)

(73) Assignee: Warner Lambert Company, Morris Plains, NJ (US)

( * ) Notice: Subject to any disclaimer, the term of this patent is extended or adjusted under 35 U.S.C. 154(b) by 337 days.

(21) Appl. No.: 10/344,482

(22) PCT Filed: Aug. 21, 2001

(86) PCT No.: PCT/EP01/09594

§ 371 (c)(1),
(2), (4) Date: Feb. 11, 2003

(87) PCT Pub. No.: WO02/17886

PCT Pub. Date: Mar. 7, 2002

(65) Prior Publication Data
US 2003/0175335 A1 Sep. 18, 2003

(30) Foreign Application Priority Data
Sep. 1, 2000 (EP) ................................. 00402423

(51) Int. Cl.
*A61K 9/52* (2006.01)
*A61K 9/48* (2006.01)

(52) U.S. Cl. .................. 424/457; 424/451; 424/452
(58) Field of Classification Search .......... 424/451–52, 424/443–44, 485, 488, 457; 514/962
See application file for complete search history.

(56) References Cited

U.S. PATENT DOCUMENTS 5,431,917 A   7/1995 Yamamoto et al.

FOREIGN PATENT DOCUMENTS

| EP | 888778 | 1/1999 |
| GB | 1559644 | 1/1980 |
| JP | 58172313 | 10/1983 |
| JP | 04027352 | 1/1992 |
| JP | 04036159 | 2/1992 |
| WO | WO0018835 | 4/2000 |

*Primary Examiner*—Susan Tran
(74) *Attorney, Agent, or Firm*—Rosemary M. Miano; Evan J. Federman

(57) ABSTRACT

The invention concerns, film-forming compositions containing pectin, at least one additional film-forming polymer and a setting system for use in pharmaceutical, veterinary, food, cosmetic or other products like films for wrapping food, aspics or jellies, preferably for predosed formulations like soft or hard capsules, as well as aqueous solutions of the composition for the manufacturing of said products.

8 Claims, 1 Drawing Sheet

PECTIN FILM COMPOSITIONS

This application claims priority from European Patent Application 00402423.8, filed Sep. 1, 2000 and PCT Application PCT/EP01/09594, filed Aug. 8, 2001.

The invention concerns film compositions containing pectin, at least one additional film-forming polymer and a setting system for use in pharmaceutical, veterinary, food, cosmetic or other products like films for wrapping food, aspics or jellies, preferably for predosed formulations like soft or hard capsules.

Preferably pectin compositions are used for manufacturing of hard capsules for pharmaceutical and veterinary applications. The pectin content of the compositions confers enteric properties to such capsules and at least one further film-forming polymer enhances the mechanical performance of the hard capsules. Combination with a setting system allows use of the film-forming compositions of the invention for industrial enteric capsule production by conventional dip moulding processes.

The use of conventional dip moulding equipment for gelatin capsule production allows the production of enteric capsules with equal dimensions and properties which can be used with conventional filling equipment for gelatin capsules.

Enteric materials have a pH-dependent solubility. They are insoluble under gastric conditions (simulated by a pH of 1.2) and readily soluble under intestinal conditions (simulated by a pH of 6.8). Generally, these materials are polymers containing carboxylic groups, such as cellulose acetate phthalate (CAP), hydroxypropyl methylcellulose phthalate (HPMCP), hydroxypropyl methylcellulose acetate succinate (HPMC-AS), acrylic copolymers, pectin or alginates.

Usually enteric properties of pharmaceutical compositions are achieved by a coating process with enteric materials on e.g. granules, pellets, tablets or hard or soft capsules.

Enteric film compositions for hard capsules are described for example in U.S. Pat. No. 4,138,013. The film-forming composition for dip moulding consists of (1) hydroxypropyl methylcellulose and an ammonium salt of cellulose acetate phthalate polymer or (2) of gelatin and an ammonium salt of a copolymer of methacrylic acid and methacrylic acid ester. However, it has been found that capsules made according to the mentioned techniques have the disadvantages of poor solubility in intestinal juice, high organic solvent content, inadequate stability and diffusion problems.

Improvements are described in EP-A-0 056 825 with film compositions containing film-forming polymers like cellulose esters or cellulose ether esters, plasticizers, viscosity-increasing substances like highly viscous cellulose ethers, and anti-foaming agents.

Conventional hard capsules are produced from gelatin by a dip moulding process. This process is based on the setting ability of hot gelatin solution by cooling. On a totally automatic industrial hard gelatin capsule machine, mould pins are dipped into hot gelatin solution, the pins are removed from the solution, inverted, the gelatin solution (gel) remaining on the pins dried, stripped off the capsule shells and finally cap and body of the capsules cut and pre-joined. The immediate setting of the gelatin solution on the mould pins after dipping is the key step in the process. Otherwise, the gelatin solution would flow down to form capsules with non-uniform wall thickness and unacceptable properties.

A further enteric film composition consisting of a mixed ester of an alkyl-, hydroxyalkyl- or hydroxyalkyl alkylcellulose esterified with succinyl anhydride and an aliphatic monocarboxylic acid anhydride is described in U.S. Pat. No. 4,365,060. However, the solutions from these compositions do not possess any setting ability and therefore are not applicable to industrial-scale dip moulding processes.

JP-A-58138458 describes a process for dipping mould pins into an aqueous solution of hydroxypropyl-methylcellulose acetate succinate alkali metal salt and gelatin and thereafter dipping in aqueous acid solution. However, in this composition the gelatin content is too low to provide sufficient setting ability to the dipping solution.

Surprisingly, we have found that film compositions based on pectin as enteric material with at least a second film-forming material and a setting system have sufficient setting ability for industrial hard capsule production.

Pectin has excellent enteric properties. A relatively low content of pectin from 5 to 25%, preferably 10 to 20% by weight in the composition, is sufficient to obtain capsule films with enteric properties. Surprisingly, the capsule of the present invention can resist dissolution at least for 2 hours in in-vitro disintegration tests at pH 1.2, and is easily soluble at pH 6.8 (>80% after 45 min under USP dissolution conditions).

The aqueous solutions of the film-forming compositions of the prior art are necessarily prepared under alkaline conditions and for this reason are quite unstable. This disadvantage is overcome by the compositions of the invention because the pectin used as enteric material is water soluble and consequently, the solution is quite stable.

Figure 1:
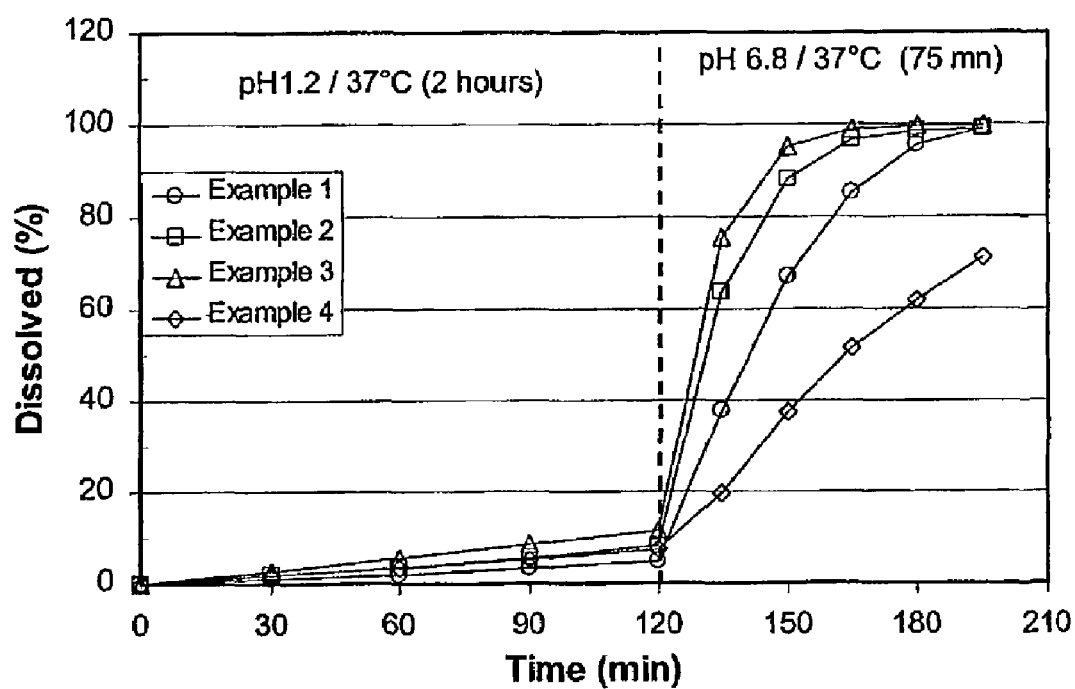
FIG. 1 describes the results of the dissolution tests.

A further advantage of pectin is that pectin itself has the properties of a setting agent as described below.

A disadvantage of pectin is its brittleness like other enteric materials, if it is used in film-forming compositions alone or in high amounts. Surprisingly, we have found that this problem could be solved by the addition of at least one further film-forming material to the film-forming composition, which may be selected generally from all hydrosoluble film-forming materials of pharmaceutical and/or food quality grade. Suitable are for example gelatin; pullulan; polyvinyl alcohol; modified starches such as hydroxypropylated starch or hydroxyethylated starch; cellulose ethers such as hydroxypropyl methylcellulose, hydroxypropyl cellulose, methylcellulose, hydroxyethyl cellulose or hydroxyethyl methylcellulose; and mixtures thereof.

Beside the improvement of the mechanical properties of the capsule film the addition of a second film-forming material also increases the content of solid material in the dip mould solution of the film composition.

The content of pectin is in the range of 5 to 60%, preferably 10 to 40%, and that of the second film-forming material in the range of 40 to 95%, preferably 50 to 85% by weight in the film composition.

Low methoxyl pectins (LM pectins) with a degree of esterification of the carboxyl groups with methanol below 50% are especially preferred.

The dipping solution for the capsule manufacturing process has a content of the film-forming composition in the range of 15 to 40% by weight.

For the production of enteric capsules by an industrial dipping process, it is essential that the dipping solution has a sufficient setting ability. Surprisingly, we have found that pectin, beside its enteric properties, can provide a sufficient setting behavior in the presence of divalent cations such as $Ca^{++}$ or $Mg^{++}$. The content of the divalent salts such as CaCl$_2$ in the dipping solution is preferably from 100 ppm to 5000 ppm (0.01 to 0.5% by weight), this means an amount of from 0.04 to 2% by weight of the final film composition. During the preparation of the solution, the formation of concentration peaks of the divalent salt has to be avoided. High local concentrations of the divalent salt will result in thermally irreversible local pectin gel formation.

The setting behavior of the film-forming solution of the invention may be also achieved or altered by the addition of further gelling agents, preferably polysaccharides such as carrageenan or gellan. It has been found that addition of a small quantity of such additional gelling agent can provide sufficient setting ability. The gelling agent content in the dipping solution is preferably from 0.05 to 2% by weight, this means an amount of from 0.2 to 8% by weight of the final film composition.

The temperature of the solution during the dipping process is also important for the setting properties of the dipping solution. Preferably the temperature should be above 50° C., and is dependent on the pectin content. It has been found that the temperature of the dipping solution has to be increased with higher pectin contents.

The inventive composition may contain in a further aspect additional pharmaceutically or food-acceptable colouring agents in the range of 0 to 10% based upon the weight of the final film composition.

The inventive composition may contain in a further aspect additional pharmaceutically or food acceptable plasticizer or flavouring agents.

Finally, the inventive film-forming solution can be used for banding enteric capsules. This prevents the capsule from leaking or separation of body and cap in gastric fluids.

The following examples and tests illustrate hard enteric capsule production with the composition from the dipping solutions of the invention and its enteric properties.

EXAMPLE 1

In 3.9 kg of deionised water at room temperature 2.5 g of CaCl$_2$ (0.05% by weight of the final dipping solution) and 100 g of glycerol (plasticizer, 2%) were dissolved, then 200 g of LM pectin (4%) and 800 g of hydroxypropyl starch (16%) dispersed. The mixture was then heated to 95° C. to solubilize all components under stirring. After debubbling by reducing the stirring, the solution was equilibrated at 60° C.

The solution was poured into a dipping dish of a pilot machine of conventional hard gelatin capsule production equipment. Keeping the dipping solution at 60° C., natural transparent hard enteric capsules of size 0 were produced according to the conventional process with the same dimensional specifications as the conventional hard gelatin capsules. The final capsules have a film composition of 16.3% pectin, 65.3% hydroxypropyl starch, 8.1% glycerol, 0.20% CaCl$_2$ and 10% moisture by weight.

EXAMPLE 2

200 g of LM pectin was dispersed into 2.0 kg of deionised water at room temperature, and then the mixture was heated to 85° C. to solubilize the pectin. After debubbling by reducing the stirring, the solution was then equilibrated at 60° C.

2.5 kg of aqueous gelatin solution at 32% was prepared by conventional method for hard gelatin capsule manufacture. 11.75 g of CaCl$_2$ aqueous solution at 20% was added to the gelatin solution, which was then debubbled by standing at 60° C.

The above two solutions were mixed together by gentle stirring to avoid creating bubbles. The solution thus prepared (containing 4.25% pectin, 17.0% gelatin and 0.05% CaCl$_2$ by weight) was then poured into a dipping dish of a pilot machine of conventional hard gelatin capsule production equipment. Keeping the dipping solution at 45° C., natural transparent hard enteric capsules of size 0 were produced according to the conventional process with the same dimension specifications as the conventional hard gelatin capsules.

The final capsules have a film composition of 16.9% pectin, 67.4% gelatin, 0.20% CaCl$_2$ and 15.5% moisture by weight.

EXAMPLE 3

250 g of polyethyleneglycol 400, pre-heated at 60° C. was added under gentle stirring into 4.7 kg solution at 60° C., containing by weight 4.25% pectin, 17.0% gelatin and 0.05% CaCl$_2$, prepared as in example 2.

Natural transparent enteric hard capsules were produced as in example 2. The final capsules have a film composition of 13.9% pectin, 55.8% gelatin, 17.4% PEG400 and 0.16% CaCl$_2$ and 12.7% moisture by weight.

EXAMPLE 4

3.85 g of gellan gum and 150 g of LM pectin were dispersed into 2.0 kg of deionised water at room temperature. The mixture was then heated to 85° C. for solubilization. After debubbling, the solution was then equilibrated at 60° C.

2.66 kg of aqueous gelatin solution containing 32% gelatin by weight was prepared by conventional method for hard gelatin capsule manufacturing and equilibrated at 60° C.

The above two solutions were mixed and debubbled. The final solution contained 3.12% pectin, 17.7% gelatin and 0.08% gellan gum by weight.

Natural hard enteric capsules of size 0 were produced in the same manner as in the previous examples, keeping the dipping solution at 55° C. The final capsules have a film composition of 12.8% pectin, 72.4% gelatin and 0.33% gellan gum and 14.5% moisture by weight.

All the capsules were evaluated for their enteric performance by in-vitro disintegration and dissolution tests according to the UPS XXIIII: first 2 hours in simulated gastric fluid (pH1.2) and then in simulated intestinal fluid (pH6.8). No enzyme was used in these tests.

The capsules were filled with lactose containing 0.1% of Indigotine (FD&C blue No2) for disintegration test or filled with acetaminophen for in-vitro dissolution test. Capsules were then banded with the same solution used respectively during the capsule manufacture for each example. The capsule banding prevents separation of capsule cap and body during the disintegration test.

The results of the disintegration tests are shown in Table 1 and the results of the dissolution tests are shown in FIG. 1.

TABLE 1

Disintegration Results

| Capsule | Disintegration time | |
|---|---|---|
| | pH1.2 | pH6.8 |
| Example 1 | >2 h | 10.6 min |
| Example 2 | >2 h | 3.5 min |
| Example 3 | >2 h | 2.5 min |
| Example 4 | >2 h | 4.8 min |

The tests performed confirmed the excellent gastric resistance of all capsules, they remained intact even after 2 hours exposition to pH 1.2.

Capsules of examples 1–3 dissolved very quickly after passing into pH 6.8 buffer solution. Capsules of example 4 showed some delay. The use of an additional setting agent would be a possibility to modulate the dissolution profile under intestinal conditions.

The invention claimed is:

1. An enteric capsule film composition consisting essentially:
   a) 5–60 weight % pectin;
   b) 40–95 weight % of a second film-forming polymer selected from the group consisting of gelatin; pullulan; polyvinyl alcohol; hydroxypropylated starch, hydroxyethylated starch; hydroxypropyl methylcellulose, hydroxypropyl cellulose, methylcellulose, hydroxyethyl cellulose, hydroxyethyl methyl cellulose; or mixtures thereof; and
   c) a setting system comprising the pectin of part (a) in combination with
      (i) 0.04–2 weight % of a salt comprising a divalent cation; or
      (ii) 0.2–8 weight % of a polysaccharide selected from the group consisting
   of carrageenan, gellan and mixtures thereof;
   wherein the capsule can resist dissolution for at least 2 hours at a PH of 1.2.

2. A capsule according to claim 1 wherein the content of pectin is 10–40%, and that of the second film-forming polymer is 50 to 85%.

3. A capsule according to claim 1 wherein the divalent cationic salts are selected from the group consisting of magnesium and calcium salts.

4. A capsule according to claim 1 additionally comprising at least one additional ingredient selected from the group consisting of coloring agents, plasticizers and flavoring agents.

5. A method for making a capsule of claim 1 wherein the method is a dip molding process using a solution at a temperature of above 50 degrees C.

6. A capsule as claimed in claim 1 wherein the second film-forming polymer is gelatin.

7. A capsule as claimed in claim 1 wherein the second film-forming polymer is hydroxypropyl methylcellulose.

8. A capsule as claimed in claim 1 wherein the second film-forming polymer is pullulan.

* * * * *